United States Patent
San George et al.

[11] Patent Number: 5,278,044
[45] Date of Patent: Jan. 11, 1994

[54] STABLE AQUEOUS NADH REAGENT AND KIT

[75] Inventors: Richard C. San George, Waltham; Carol A. Adiletto, Melrose, both of Mass.

[73] Assignee: Instrumentation Laboratory, S.p.A., Milan, Italy

[21] Appl. No.: 917,789

[22] Filed: Jul. 20, 1992

Related U.S. Application Data

[63] Continuation of Ser. No. 544,584, Jun. 27, 1990, abandoned.

[51] Int. Cl.$^5$ ............................................. C12Q 1/32
[52] U.S. Cl. ................................... 435/26; 435/4; 435/6; 435/810; 435/975; 435/15; 436/17
[58] Field of Search ................... 435/4, 6, 26, 15, 810, 435/975; 436/17

[56] References Cited

U.S. PATENT DOCUMENTS

| | | | |
|---|---|---|---|
| 4,153,511 | 5/1979 | Modrovich | 195/99 |
| 4,271,264 | 6/1981 | Modrovich | 435/14 |
| 4,277,562 | 7/1981 | Modrovich | 435/17 |
| 4,310,624 | 1/1982 | Modrovich | 435/4 |
| 4,372,874 | 2/1983 | Modrovich | 435/4 |
| 4,394,449 | 7/1983 | Modrovich | 435/188 |

FOREIGN PATENT DOCUMENTS

| | | |
|---|---|---|
| 0009222 | 4/1980 | European Pat. Off. |
| 53-107486 | 9/1978 | Japan |
| 8047879 | 12/1980 | Japan |
| 1153109 | 5/1969 | United Kingdom |

OTHER PUBLICATIONS

W. Gerhardt et al, "Quality Control of NADH" Scand. J. of Clin & Lab Invest., vol. 33, pp. 1–51 (1974).
S. A. Margolis et al, "Purification & Analysis of the Purity of NADH", Clin. Chem., vol. 22, No. 8, pp. 1322–1329(1976).
D. Northrup et al, "Purification of Reduced Nicotinamide . . . " Methods In Enzymology, vol. 122, pp. 152–154 (1986).
Beckman Instruments Inc., "Beckman Liquid-Stat (R) Reagent AST" (1987).
Beckman Instruments Inc., "Beckman Liquid-Stat (R) Reagent ALT" (1987).
Chem. Abstract 104:84922d (1986).
Chem Abstr 84:175661c (1976).

Primary Examiner—Ronald W. Griffin
Assistant Examiner—Pamela S. Webber
Attorney, Agent, or Firm—Testa, Hurwitz & Thibeault

[57] ABSTRACT

An aqueous coenzyme reagent composition contains NADH, a carbonate/bicarbonate buffer (with a pH of about 9.5-11) and water. Both NADH and the buffer are at low concentrations, e.g., about 2-5 mM for NADH and about 2-15 mM for carbonate/bicarbonate. When this coenzyme reagent is mixed with an enzyme reagent, the mixture achieves a neutral pH. The combination of high pH, low NADH concentration and low buffer concentration permit the aqueous reagent to be stored for extended periods at low temperatures without NADH degrading to form impurities which interfere with or inhibit enzyme activity, such as the activity of lactate dehydrogenase or malate dehydrogenase in an assay for ALT or AST.

17 Claims, No Drawings

STABLE AQUEOUS NADH REAGENT AND KIT

This is a continuation of copending application Ser. No. 7,544,584 filed on Jun. 27, 1990, now abandoned.

The present invention relates to diagnostic reagents and kits for detecting constituents of biological fluids, and particularly to those reagents and kits which, in use, oxidize NADH to NAD+.

The oxidation of the coenzyme nicotinamide adenine dinucleotide from its reduced form (commonly abbreviated NADH) to its oxidized form (commonly abbreviated NAD+) occurs during a variety of in vivo and in vitro enzymatic processes. Exemplary are the action of the enzyme lactate dehydrogenase (LDH) to reduce pyruvate to lactate with the concombinant oxidation of NADH to NAD+.

Diagnostic kits make use of such enzymatic reaction to determine constituents directly participating in such reactions (e.g., LDH determination), but also to determine constituents that affect such reactions indirectly. For example, alanine aminotransferase (ALT) is assayed by a kit which includes, overall: alanine, alpha-ketoglutarate, LDH, NADH and various salts and buffers. Similarly, aspartate aminotransferase (AST) is assayed by a kit which includes, overall: aspartate, alpha-ketoglutarate, malate dehydrogenase (MDH), LDH, NADH and various salts and buffers. Similar kits are well known for assaying LDH, total carbon dioxide (TCO2), triglycerides, urea (BUN) and a variety of other enzymes and enzymatic substrates.

To provide useful stability to the kits between manufacture and use, it has been generally necessary to lyophilize one or more constituents, and especially to lyophilize any reagent containing NADH. Typically, lyophilized NADH, stored in a fashion to be kept free of moisture, is later reconstituted separately because of its limited liquid stability. Upon degradation, not only is NADH coenzyme activity lost, but more importantly degradation products are formed which interfere with or inhibit the desired reactions. See W. Gerhardt et al, "Quality Control of NADH" Scand. J. of Clin. & Lab. Invest., vol. 33, pp. 1-51 (1974). Thus, in particular, NADH which has degraded only in small proportion will inhibit LDH activity upon use.

U.S. Pat. No. 4,394,449 to Modrovich (1983) proposes dividing each kit into one solution with all reagents except NADH and a second reagent solution (called the coenzyme reagent solution) containing NADH and a diol (e.g, 1,2-propanediol), wherein the coenzyme reagent solution is rigorously water free. Shortly before use, the coenzyme reagent solution is combined with the remaining reagents. Unfortunately, the diol also acts as an enzyme inhibitor (especially of LDH) and thus must be highly diluted when mixing. Thus high mixing ratios (20:1 or greater) are required, so that high NADH concentrations in the coenzyme reagent solution (e.g., 10 mM NADH) are also required.

BRIEF DESCRIPTION OF THE INVENTION

It has been found that NADH may be kept for long periods without degradation in an aqueous solution, provided that the pH is high (e.g., 9.5 to 11 and especially 10.0 to 10.4), the NADH concentration is low and the buffer system is carefully selected. Since the working pH of the enzymatic reaction is typically lower (e.g., 6-8), buffer concentration should also be minimized so that the high pH of this reagent can be neutralized when it is mixed with other reagents. Lowered buffer concentration also improves NADH stability. An alkali metal carbonate/bicarbonate buffer system has been selected, although ammonium carbonate/bicarbonate can also be used with certain tests. For other tests, such as AST and ALT, ammonium ions contributed to the working reagent by the NADH composition may provide other interferences under many conditions.

Thus, the present invention provides in one form, a kit for determining a constituent of a biological sample, the constituent affecting directly or indirectly an enzymatic reaction for which NADH is a coenzyme, comprising:

a) one reagent containing coreactants for the reaction sequence affected by the constituent being determined, and b) as an additional reagent, an aqueous solution containing NADH at a concentration of about 1 to 4 mM and an alkali metal or ammonium bicarbonate buffer at a concentration of about 2 to 15 mM, the aqueous solution having a pH of about 9.5 to 11.0.

The present invention also provides, in another form, an aqueous composition, useful as a diagnostic coenzyme reagent, comprising water, NADH at a concentration of about 1 to 4 mM and an alkali metal carbonate/bicarbonate buffer at a concentration of 2 to 15 mM, the aqueous composition having a pH of about 9.5 to 11.0.

DETAILED DESCRIPTION OF THE INVENTION

The present aqueous NADH solution is selected for long term stability, especially at storage temperatures such as 0-5 deg C. The solution contains water, buffers and NADH and, preferably, is limited to these ingredients. Thus, the solution preferably consists essentially of these three ingredients.

The NADH used is preferably of high purity (98% or better) and should be substantially free of degradation products of the type that inhibit LDH activity. An exemplary material is available from Boehringer Mannheim as BMD Grade II. Methods of purifying NADH are well known, and are exemplified by the anion exchange HPLC procedures described in C. J. Newton et al, Anal. Biochem., vol. 132, 50 (1983) and G. A. Orr et al, Anal. Biochem., vol. 142, 232 (1984) and the reverse phase HPLC procedures describe in S. A. Margolis et al, Clin. Chem., vol. 22, 1322 (1976). NADH is present in the composition at a concentration of about 1 to about 4 mM, and especially at about 2 mM.

The water used in the composition should be of high purity, and can be deionized water of diagnostic grade. Impurities in the water that should be avoided include polybasic anions such as phosphates, arsenates and sulfates and monobasic anions such as acetates. For many tests such as ALT and AST, ammonium ions should also be avoided.

The buffer system used to establish the high pH of the solution should be of the carbonate-bicarbonate type, with alkali metal carbonate/bicarbonate (especially sodium or potassium) being more preferred and ammonium carbonate-bicarbonate being somewhat less preferred. Once a desired pH is determined, it can be achieved by using an appropriate ratio of the carbonate and bicarbonate salts (e.g., of disodium carbonate to sodium bicarbonate). Since the NADH is at a relatively low concentration, the mixing ratio with the other reagents and sample will also be low. Accordingly, the total concentration of buffer salts should be low so that the high pH of the aqueous solution can be neutralized down to the neutral pH range where enzyme activity is optimized. For this reason, the total concentration of buffer salts (e.g., of disodium carbonate and sodium bicarbonate) is relatively low, in the range of about 2 to 15 mM, preferably about 3 to 8 mM and especially about 5 mM. This low buffer concentration is also important in maintaining the stability of NADH (whose degradation exhibits general acid-catalysis).

The pH of the aqueous solution has been found to significantly affect NADH stability. NADH degrades over time if the pH is too low or if the pH is too high. The most preferred range of pH 10.0 to 10.4 (especially for sodium carbonate/bicarbonate buffer) has been selected to minimize NADH degradation to form impurities that inhibit enzyme activity (e.g., LDH activity).

While, in general, no other ingredients which actively participate in the enzymatic reactions should be present in this aqueous solution, various minor ingredients (especially salts) can be present. Any such salts that are present should, however, be preferably of low concentration such that ionic strength remains low.

In addition to the aqueous solution containing NADH, the diagnostic kit contains one or more other reagents. These reagents and the sample together provide the constituent necessary for the enzymatic reaction or series of enzymatic reactions by which NADH is oxidized to NAD+ as a function of the amount of the constituent of interest in the sample. This principle will be illustrated first for kits to determine ALT.

In an ALT kit, the second reagent may contain alanine, alpha-ketoglutate (AKG), LDH and various salts. That second reagent is buffered with a buffer system at a higher concentration and lower pH than the aqueous coenzyme reagent. An example is:

| | |
|---|---|
| Alanine | 300 mM |
| AKG | 37 mM |
| LDH | 2720 IU/L |
| Tris | 100 mM |
| Water | balance | with a pH of 7.6.

The above reagent can be stored for extended periods after lyophilization, and may have long stability in liquid form at 0 to 5 deg C. An aqueous reagent of the following composition can be stored for extended periods at 0 to 5 deg C:

| | |
|---|---|
| NADH | 2 mM |
| Sodium carbonate | 1.6 mM |
| Sodium bicarbonate | 3.4 mM |
| Water | balance |

When the two are combined in a volume ratio of 2.75:1, the high buffer concentration (at a pH of 7.6) in the LDH-containing reagent neutralizes the high pH from 10.0 down to 7.6 for the final working reagent. The small volume of sample (15 ul) (normally also at or near neutral pH) has no significant effect on the final pH of the reaction mixture.

An exemplary composition for the other reagent in an AST kit is given below:

| | |
|---|---|
| LDH | 820 IU/L |
| MDH | 2040 IU/L |
| AKG | 41 mM |
| Asp | 180 mM |
| Tris | 253 mM, pH 7.6 |
| Water | balance. |

Similar reagents, each useful with the common aqueous reagent (containing NADH and carbonate buffer), can be developed for each other test (such as LDH, TCO2, BUN and triglycerides) through no more than routine experimentation. Thus, the final concentration of enzymes, substrates, NADH and salts and the final pH of the mixture of sample and both reagents (7.6 in the exemplary formulations) with the two liquids can be the same or similar to those final concentrations and final pH achieved when lyophilized NADH is used.

While, in some forms of the invention, all enzymes and substrates (other than the NADH coenzyme) are in a single reagent, in other forms, two or more other reagents are used. For example, alpha-keto-glutarate (AKG) is capable of undergoing non-enzymatic transamination with other ingredients, such as apartate in the AST reagent. Such a degradation reaction may be avoided by packaging the AKG as a third reagent. While optimum concentrations for a separate AKG reagent have not been developed, it is believed that 218 mM AKG in water (buffered in 311 mM Tris to pH 7.6) will be satisfactory.

Mixing the sample, the NADH-containing aqueous reagent, the enzyme-containing reagent, (and the AKG-containing reagent, if present) with the sample can be performed manually. Preferably, however, the sample and the various reagents are pipetted or otherwise transferred into a reaction chamber or reaction/analysis chamber by an automated instrument. It is preferred to use systems of the type described in U.S. Pat. Nos. 4,738,825 and 4,788,150, which pipette into the inner and outer chambers of cuvettes in a centrifugal rotor and then, after each cuvette is loaded, spin the rotor to cause the sample or reagent in each inner chamber to overflow a dam and mix with the sample or reagent in the corresponding outer chamber. In kits having an enzyme-reagent and an NADH-reagent, it is preferred to load the NADH reagent into the inner chamber [with the sample] and the enzyme reagent into the outer chamber. In kits having an enzyme-reagent, an NADH-reagent and an AKG-reagent, it is preferred to mix the AKG-reagent with the enzyme reagent into a reagent container which is placed onto the instrument, as is a reagent container having the NADH reagent. For each test, the instrument would load NADH reagent into the inner chamber and combined enzyme-reagent and AKG-reagent into the outer chamber of each cuvette of the rotor where such a test is being performed.

The containers in which each reagent is stored are preferably of the type shown in U.S. Pat. No. 4,764,342 (sold commercially by the assignee's Instrumentation Laboratory division as BoatIL containers). Compared to the use of a single container into which both enzyme-solution and lyophilized NADH have been added, the present invention requires one or two additional reagent containers on board the instrument for a single test. It should be appreciated, however, that a single aqueous NADH reagent in a single container can be used for multiple tests (e.g., in combination with one enzyme-reagent for ALT and in combination with another enzyme-reagent for AST). Thus while two containers may be required on the carousel for a single test (e.g., ALT) to be performed, enabling additional tests (e.g., AST, LDH, BUN, TCO2 and triglycerides) would require only one additional reagent container each. If AKG is provided as a separate reagent (in a similar container), it can also be used for several different tests by mixing into separate enzyme-reagents for each test (e.g., one for ALT and one for AST).

The present invention is illustrated by the following Examples.

EXAMPLE 1

LDH Assay

Two reagents were prepared for measurement of LDH activity. The first reagent was 0.963 mM monosodium pyruvate (MW 110.0) in water at pH 7.0 with 118.75 mM phosphate salts (9.773 g/L disodium hydrogen phosphate and 6.793 g/L monopotassium dihydrogen phosphate). Four parts of this first reagent (typically 8 ml) were mixed with one part of the second reagent (typically 2 ml) containing 1 mM NADH and 5 mM ammonium bicarbonate (pH 10.0). In Example 3, below, such ammonium bicarbonate was replaced by a mixture of disodium carbonate and sodium bicarbonate. This mixture was then used on the centrifugal analyzer (MONARCH or MULTISTAT III) with 5 ul sample and 15 ul sample diluent in the inner compartment and 200 ul reagent (the mixture) and 10 ul reagent diluent in the outer compartment. Thus, the final concentrations included 0.174 mM NADH, 0.670 mM pyruvate and 82.61 phosphate in 230 ul total volume.

Samples evaluated included commercial serum controls (SeraChem level 1, SeraChem level 2 and Sigma Multi-Enzyme Lintrol (1%, 2%, 5% and 10%). Also evaluated were dilutions (10, 30, 50 and 60%) of a stock solution of D-LDH from *Staphylococcus epidermidis* from Amano Company (which contains D-LDH). In each case the measured LDH value using standard software for fresh reagents was taken as 100%. Decline in measured values with storage of the NADH reagent for various times at various temperature was monitored. At the end of each storage period, an aliquot of the NADH reagent was taken and mixed with fresh pyruvate reagent, before being tested on the anaylzer. With NADH reagent stored at 4 deg C., the values obtained indicated 8.3%, 7.6%, 5.6% 2.6% and 7.8% inhibition (on average for the various "samples") after 1 month, 2.5 months, 7 months, 15 months and 28 months. With NADH reagent stored at 15 deg C., the values obtained indicated 5.2%, 4.4%, 5.8%, 8.3% and 35.8% inhibition over the same five intervals. With NADH reagent stored at 25 deg C., the values obtained indicated 0.1%, 5.1% and 48.8% inhibition after 1, 2.5 and 7 months, respectively. With NADH stored at 37 deg C., the values obtained indicated 2.4% and 65% inhibition after 1 and 2.5 months. With NADH stored at 50 deg C., the values obtained indicated 12.8% and 96.0% inhibition after 1 and 2.5 months.

COMPARATIVE EXAMPLE 2

The procedures of Example 1 were followed except that the NADH reagent used (in a 1:40 ratio with the first reagent described above) was 10 mM NADH in propanediol. The values obtained indicated 21.8%, 23.2% and 29.5% inhibition, respectively, after 1, 6 and 13.5 months storage at 4 deg C. and 29.2% and 68.8% inhibition, respectively, after 1 and 6 months storage at 37 deg C. Similar results were obtained using this propanediol-based NADH reagent (see U.S. Pat. No. 4,394,449) and the commercially-available MAS formulation which is believed to be based on that patent.

EXAMPLE 3

The procedures of Example 1 were repeated using sodium bicarbonate in place of ammonium bicarbonate in the NADH reagent (still maintaining a pH of that reagent of 10.0). With the modified NADH reagent stored at 4 deg for 3 and 23.5 months, the values obtained indicated 4.9% and 8.0% inhibition, respectively. With the modified NADH reagent stored at 37 deg C. for 3 months, the values obtained indicated 21.4% inhibition. With the modified NADH reagent stored at 50 deg C. for 1 and 2.5 months, the values obtained indicated 6.2% and 88.9% inhibition, respectively.

EXAMPLE 4

AST Assays

The ammonium bicarbonate/NADH reagents made in Example 1, both fresh and after storage at 4 deg C and 15 deg C, were evaluated in AST assays using the AKG/aspartate/enzyme reagent described above. On the MONARCH instrument, each inner compartment was loaded with 15 ul sample (one of the SeraChem or Lintrol serum controls), 25 ul diluent and 40 ul of the NADH reagent; each outer compartment was loaded with 110 ul of AST reagent and 10 ul diluent. Compared to results with fresh ammonium bicarbonate/NADH reagent, results with such reagent stored at 4 deg C for 28 months recovered 102% (indicated AST concentration 2% higher) and results with such reagent stored at 15 deg C for 28 months recovered 93% (indicated AST concentration 7% lower). After storage at 4 deg C for 28 months, the results showed linearity up to 70% Lintrol or 400 U/L; after storage at 15 deg C for 28 months, the results showed linearity up to 50% Lintrol or 275 U/L (linearity experiments were assayed at 30 deg C).

EXAMPLE 5

ALT Assay

The ammonium bicarbonate/NADH reagents made in Example 1, both fresh and after storage at 4 deg C, were evaluated in ALT assays using the AKG-/alanine/enzyme reagent described above. On the MONARCH instrument, each inner compartment was loaded with 15 ul sample (one of the SeraChem or Lintrol serum controls), 25 ul diluent and 40 ul of the NADH reagent; each outer compartment was loaded with 110 ul of the ALT reagent and 10 ul diluent. Compared to results with fresh ammonium bicarbonate/-NADH reagent, results with such reagent stored at 4 deg C for 28 months recovered 98% (indicated ALT concentration 2% lower). Linearity studies on the reagent stored at 4 deg C for 28 months showed linearity to 70% Lintrol or 400 U/L. Again, the assay was performed at 30 deg C.

EXAMPLE 6

AST Assays

The sodium bicarbonate/NADH reagents made in Example 3, both fresh and after storage at 4 deg C for 24 months, were evaluated in the same AST assays described in Example 4 with the same controls as "sample". The recovery for the experiment with reagent stored at 4 deg C yielded 103% recovery (a 3% higher value than with fresh NADH reagent). Both fresh NADH reagent and reagent stored at 4 deg C showed linear results with various Lintrol standards up to 70% (up to 375 IU/L of AST). Again, the assay was performed at 30 deg C.

EXAMPLE 7

ALT Assays

The sodium bicarbonate/NADH reagents made in Example 3, both fresh and after storage at 4 deg C for 24 months, were evaluated in the same ALT assays described in Example 5 with the same controls as "sample". The results indicated 102% recovery (a 2% higher value for the test with stored NADH reagent compared to the test with fresh NADH reagent). Both fresh and stored NADH reagent gave linear results up to 70% Lintrol standard (375 IU/L of ALT).

EXAMPLE 8

Concurrent AST And ALT Assays

Three separate reagents were loaded into BoatIL containers on the MONARCH instrument:

AST-1

40.9 mM AKG, 178.8 mM L-aspartate, 2040 IU/L MDH, 816 IU/L LDH, 253.0 mM Tris base (pH 7.6).

ALT-1

37.3 mM AKG, 297.8 mM L-alanine, 2720 IU/L LDH, 100.6 mM Tris base (pH 7.6).

NADH-2

2 mM NADH, 5 mM sodium bicarbonate (pH 10.0).

For each of AST-1 and ALT-1, the AKG reagent was prepared separately and then loaded into a common BoatIL container with either aspartate, MDH, LDH and Tris base (for AST-1) or alanine, LDH and Tris base (for ALT-1). For purposes of evaluating the stability of the AKG reagent, the AKG reagent and the other components of AST-1 and of ALT-1 were stored for 52 days (at 4 deg C and at 52 deg C) before being combined in a BoatIL container on the day of the test.

The instrument was set up to load into each cuvette on a common rotor where an AST test was to be performed: 15 ul sample, 25 ul diluent and 40 ul of freshly-prepared NADH-2 reagent (all in the inner compartment) and 110 ul reagent AST-1 and 10 ul buffer (all in the outer compartment). The instrument was set up to load into each cuvette on a common rotor where an ALT test was to be performed: 15 ul sample, 25 ul diluent and 40 ul of freshly prepared NADH-2 (all in the inner compartment) and 110 ul reagent ALT-1 and 10 ul buffer (all in the outer compartment). In this fashion, tests for both AST and ALT were performed on common "samples" (SeraChem level 1 and level 2 controls) with the following results:

AST Results

Comparing results with fresh AST-1 reagent and results where the components of the AST-1 reagent were stored at 4 deg C for 52 days, the stored reagents recovered 100.6% of the AST values of the fresh reagent (were 0.6% higher). When the components of the AST-1 reagent were stored at 37 deg C for 52 days, the assay recovered 103.7% of the AST values of fresh reagent (was 3.7% higher). These recoveries represent an average of a panel of Multi-Enzyme Lintrol dilutions and Serachem 1 and 2 controls. Linearity was demonstrated to 100% Lintrol or about 560 U/L of AST (analysis at 30 deg C).

ALT Results

Components of the ALT-1 reagent stored at 4 deg C for 52 days before being combined in a BoatIL container recovered 98.8% of the ALT values of the fresh reagent (were 1.2% lower). Components of the ALT-1 reagent stored at 37 deg C for 52 days recovered 102.3% of the ALT values of fresh reagent (were 2.3% higher). These recoveries represent an average of a panel of Multi-Enzyme Lintrol dilutions and Serachem 1 and 2 controls. Linearity was demonstrated to 100% Lintrol or about 570 U/L of ALT (analysis at 30 deg C).

We claim:

1. A kit for determining the presence of a constituent in a biological sample wherein oxidation of NADH to $NAD^+$ is indicative of the presence of the constituent, consisting essentially of:
   a) a first reagent consisting essentially of at least one compound which reacts with the constituent being determined thereby inducing the oxidation of NADH to $NAD^+$, and
   b) a second reagent consisting essentially of an aqueous solution of NADH at a concentration of about 1 to 4 mM and a buffer selected from the group consisting of: alkali metal carbonates, alkali metal bicarbonates, ammonium carbonates, ammonium bicarbonates and mixtures thereof, the buffer having a concentration of from about 2 to 15 mM, wherein the aqueous solution has a pH of about 9.5 to 11.0.

2. The kit of claim 1 wherein the buffer concentration is in the range of from about 3 mM to about 10 mM.

3. The kit of claim 1 wherein the buffer is a mixture of an alkali metal carbonate and an alkali metal bicarbonate.

4. The kit of claim 3 wherein the alkali metal carbonate is sodium carbonate and the alkali metal bicarbonate is sodium bicarbonate.

5. The kit of claim 4 wherein the sodium carbonate and bicarbonate together have a concentration of about 5 mM and a pH of about 10.0 to about 10.5.

6. The kit of claim 1 wherein the first reagent contains lactate dehydrogenase, alanine and alphaketoglutarate and wherein the constituent being determined is ALT.

7. The kit of claim 1 wherein the first reagent contains lactate dehydrogenase, maleate dehydrogenase, alphaketoglutarate and aspartate, and wherein the constituent being determined is AST.

8. The kit of claim 7 wherein the alphaketoglutarate is packaged as a separate third reagent.

9. The kit of claim 1 wherein the second reagent consists essentially of:
   i) NADH at a concentration of about 1 to 4 mM,
   ii) an alkali metal carbonate,
   iii) an alkali metal bicarbonate, the alkali metal carbonate and bicarbonate together having a concentration of about 3 to 10 mM, and
   iv) water.

10. The kit of claim 9 wherein the alkali metal carbonate is sodium carbonate and the alkali metal bicarbonate is sodium bicarbonate.

11. The kit of claim 10 wherein the sodium carbonate and bicarbonate together have a concentration of about 5 mM and a pH of about 10.0 to about 10.5.

12. The kit of claim 9 wherein NADH has a concentration of about 2 mM.

13. An aqueous composition, useful as a diagnostic coenzyme reagent, consisting essentially of water, NADH having a concentration of about 1 to 4 mM and a mixture of an alkali metal carbonate buffer and an alkali metal bicarbonate buffer having a concentration of about 2 to 15 mM, the aqueous composition having a pH of about 9.5 to 11.0.

14. The aqueous composition of claim 13 wherein the pH is from about 10.0 to about 10.5.

15. The aqueous composition of claim 13 wherein the alkali metal carbonate is sodium carbonate and the alkali metal bicarbonate is sodium bicarbonate.

16. The aqueous composition of claim 13 wherein buffer concentration is in the range of from about 3 to about 10 mM.

17. The aqueous composition of claim 13 wherein the concentration of NADH is about 2 mM.

* * * * *